[19] United States Patent
Ivanov

[11] 4,425,915
[45] Jan. 17, 1984

[54] SURGICAL CLIP APPLIER WITH IN-LINE CARTRIDGE AND INTERRUPTABLE BIASED FEEDER

[75] Inventor: Konstantin Ivanov, Edison, N.J.

[73] Assignee: Ethicon, Inc., Somerville, N.J.

[21] Appl. No.: 352,832

[22] Filed: Feb. 26, 1982

[51] Int. Cl.³ ............................................. A61B 17/12
[52] U.S. Cl. ..................................... 128/325; 227/19; 227/DIG. 1; 227/125
[58] Field of Search .................. 128/325, 326, 334 R, 128/335, 335.5, 346; 227/DIG. 1, DIG. 1A, DIG. 1B, DIG. 1C, 19, 117, 125; 29/243.56; 72/410

[56] References Cited

U.S. PATENT DOCUMENTS

| 2,479,190 | 8/1949 | Wheeler | 227/117 |
| 3,006,344 | 10/1961 | Vogelfanger | 128/346 |
| 3,753,438 | 8/1973 | Wood et al. | 128/346 X |
| 4,201,314 | 5/1980 | Samuels et al. | 227/DIG. 1 |
| 4,299,224 | 11/1981 | Noiles | 128/325 |
| 4,325,376 | 4/1982 | Klieman et al. | 128/335 X |
| 4,361,229 | 11/1982 | Mericle | 128/325 X |
| 4,372,316 | 2/1983 | Blake et al. | 128/325 |

FOREIGN PATENT DOCUMENTS 2054026 2/1981 United Kingdom ............... 128/326

Primary Examiner—C. Fred Rosenbaum
Assistant Examiner—Michelle N. Lester
Attorney, Agent, or Firm—Robert L. Minier

[57] ABSTRACT

An instrument is provided for applying ligating clips from a magazine. The magazine has an open rear end and an open front end. A toothed pusher bar is urged forwardly by a spring into the magazine to push a row of clips forwardly so as to position one clip between a pair of jaws. The jaws are actuated to close the clip by a pair of scissors-type handles. As the scissors-type handles are closed, a toothed pawl carried on one of the handles engages the teeth on the pusher bar to disengage the pusher bar from the last clip in the magazine so as to eliminate the imposition of undesirable forces on the row of clips in the magazine during the application of the front clip.

19 Claims, 12 Drawing Figures

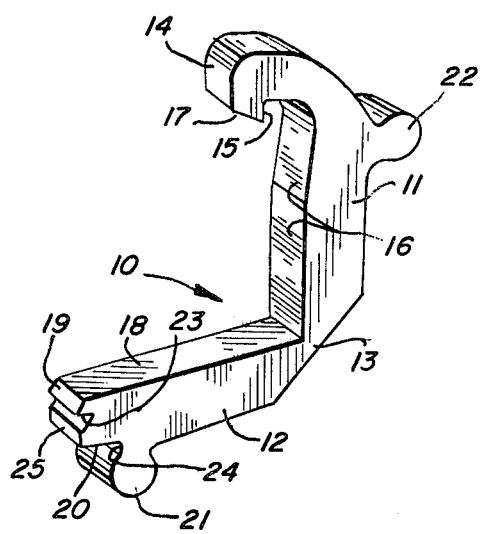
FIG. 1A
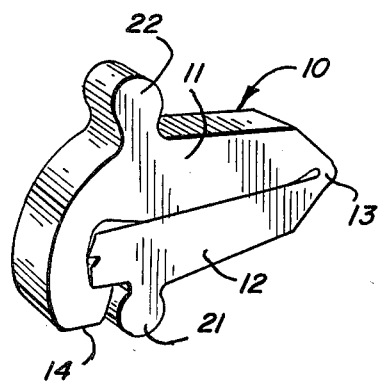
FIG. 1B
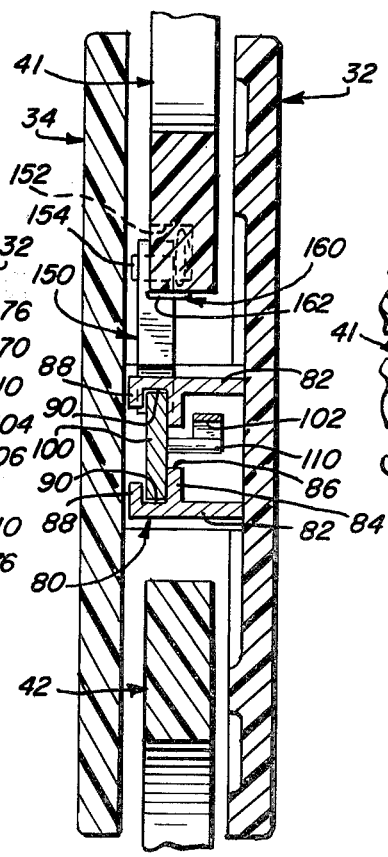
FIG. 4
FIG. 6A
FIG. 6B

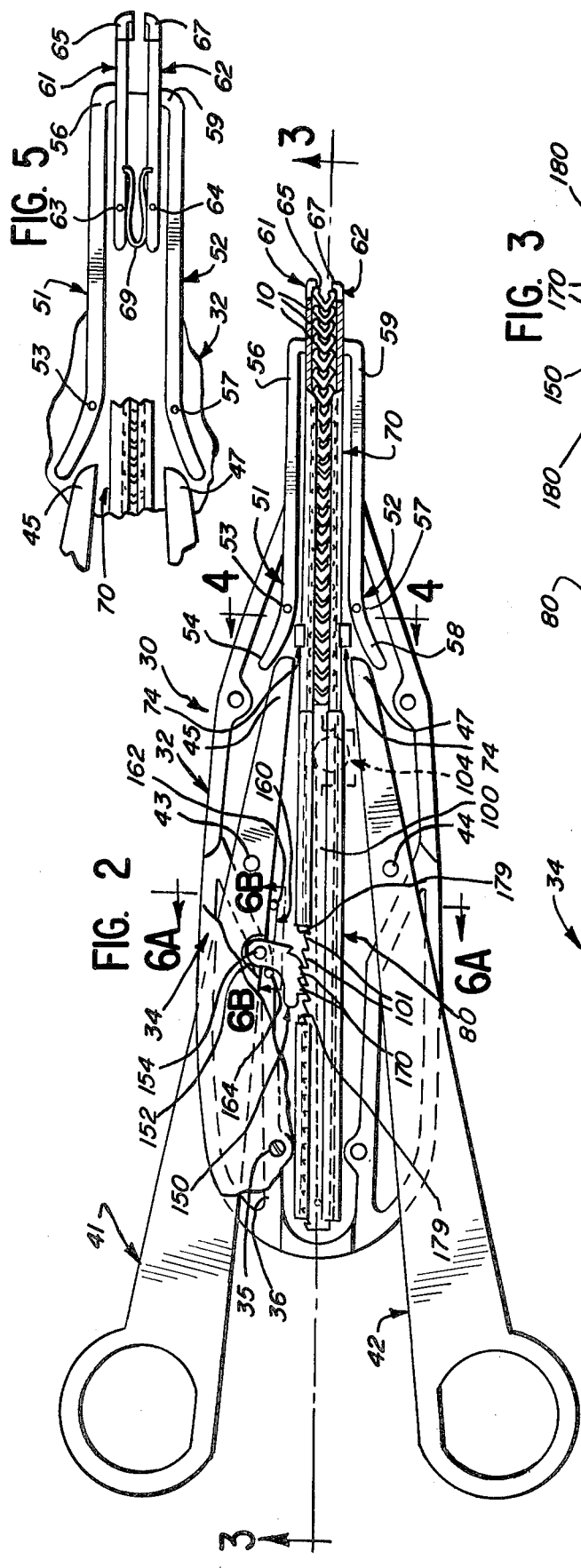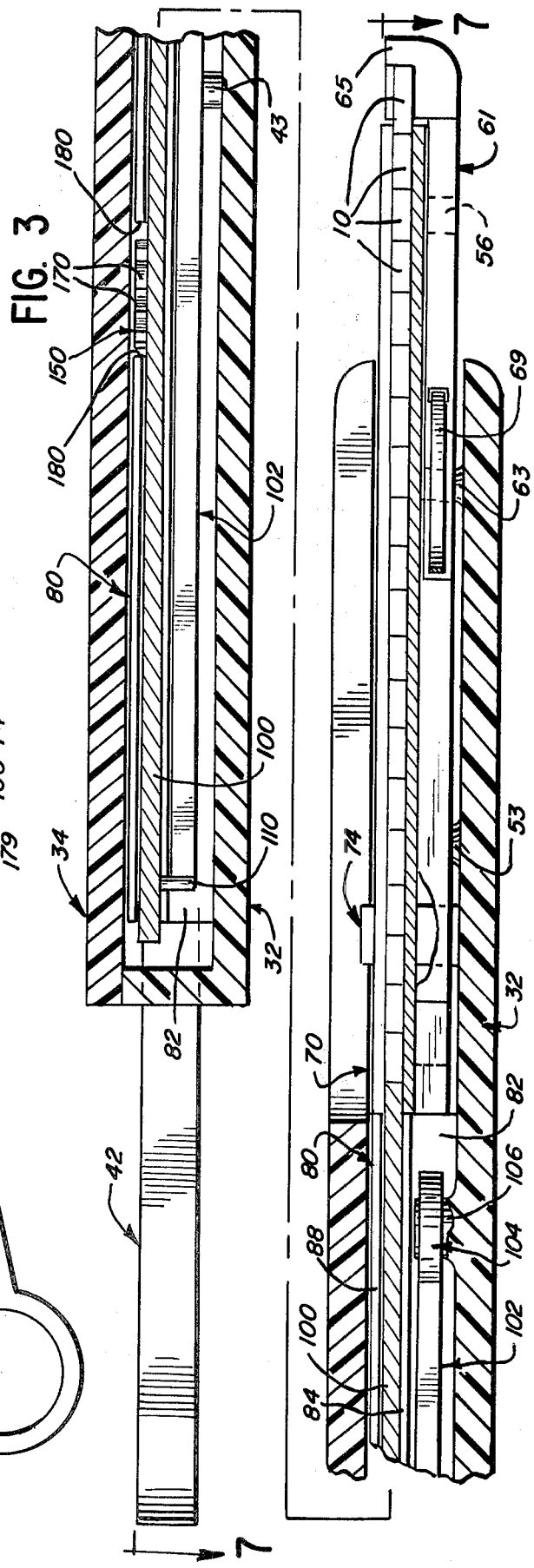

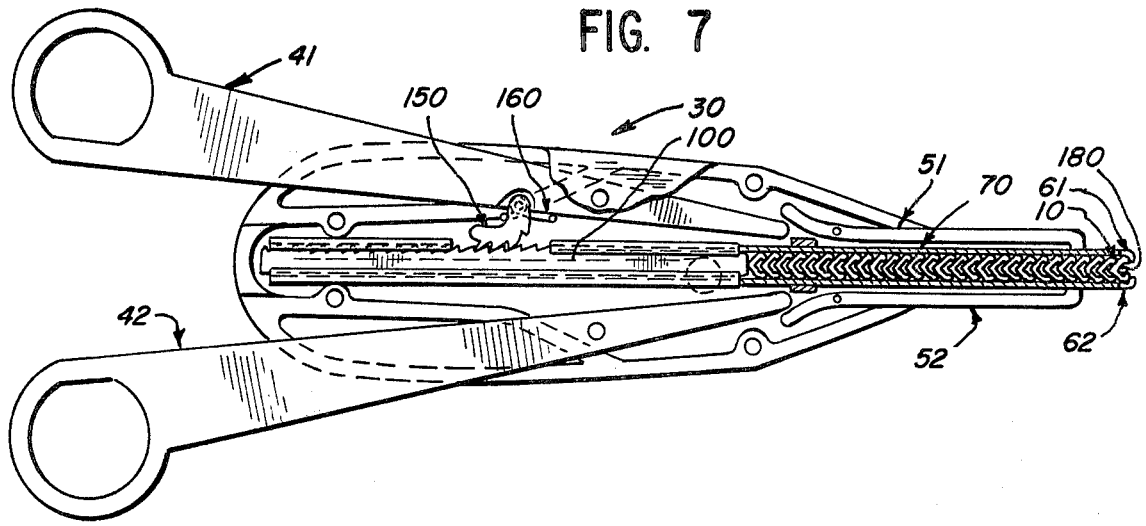
FIG. 7
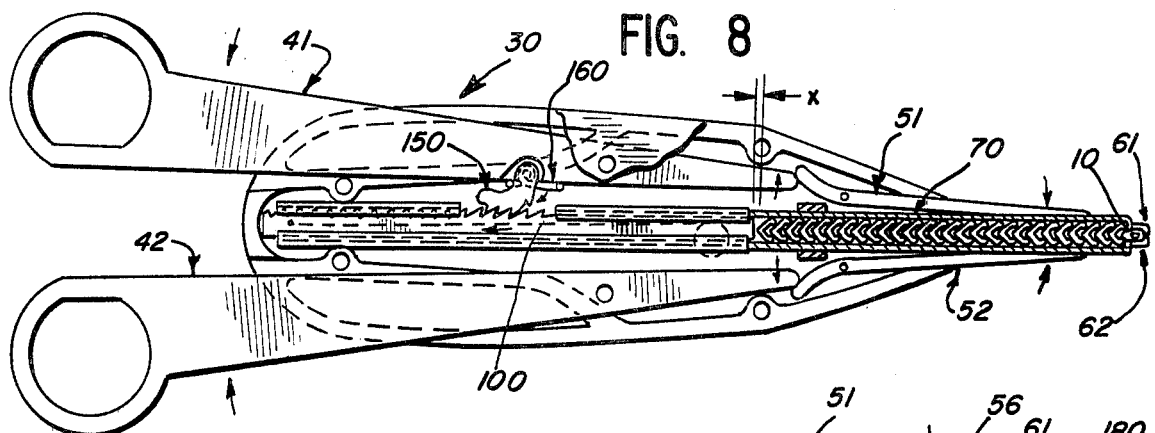
FIG. 8
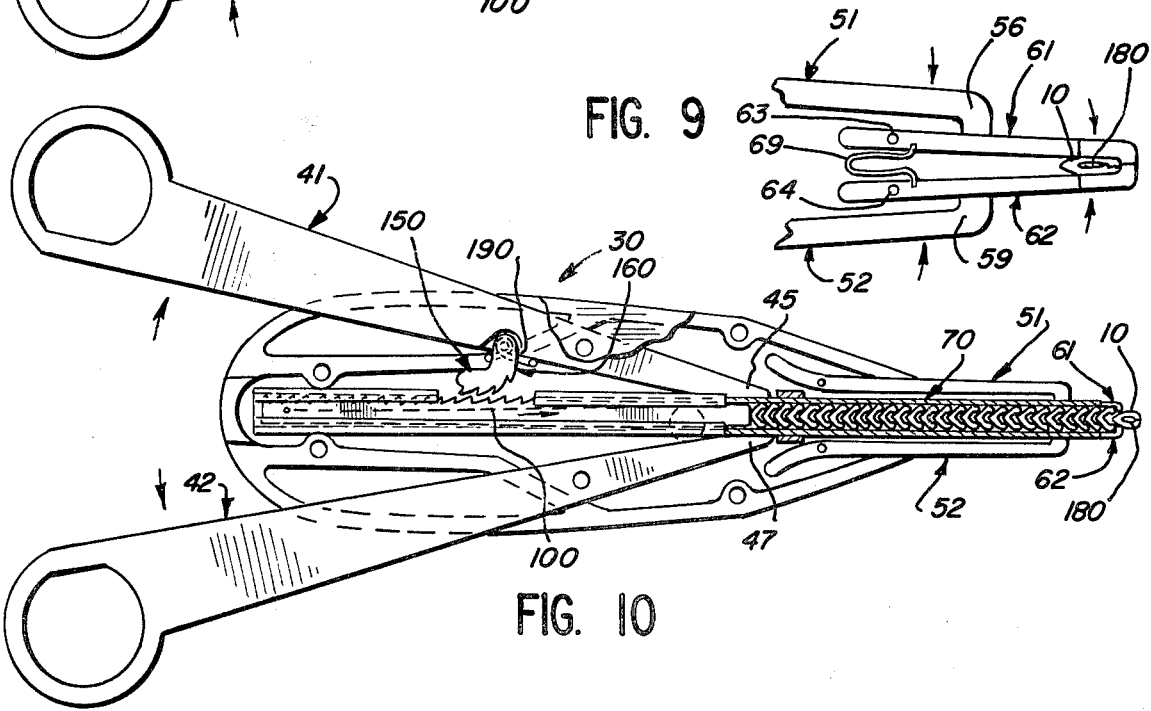
FIG. 9
FIG. 10

SURGICAL CLIP APPLIER WITH IN-LINE CARTRIDGE AND INTERRUPTABLE BIASED FEEDER

TECHNICAL FIELD

This invention relates to a surgical instrument for repeatedly applying surgical clamps or clips to tissue, blood vessels, and the like.

BACKGROUND OF THE INVENTION

Clips have been devised for clamping or strangulating various organs, vessels, and other tissue. Clips have been developed for use specifically in strangulating blood vessels in the human body. Such clips are known as hemostatic or ligating clips. The clips may be fabricated from absorbable or nonabsorbable polymeric materials as well as from metal.

A ligating clip is typically C-shaped, U-shaped, or V-shaped with two spaced-apart or diverging legs connected together at one end in a manner that permits the clip to be squeezed together so that the legs of the clip may be clamped around the tissue or blood vessel so as to tightly constrict the tissue or blood vessel. This prevents a substantial amount of fluid from passing through the tissue or blood vessel from one side of the closed clip to the other side of the closed clip.

Typically, the clip is made of a material and/or has a configuration that enables the clip, once it has been forced closed, to remain set or latched and maintain the closed orientation without outside intervention. For example, if the clip is made from a metal material, the clip can be deformed to the closed position. If the clip is made from a thermoplastic material, the legs may be connected by a resilient hinge portion and the distal ends of the legs may be provided with latch means for holding the legs together in a closed position when the legs of the clip are squeezed together around the tissue or blood vessel.

A variety of instruments for applying such surgical clips have been developed or proposed in the past. A number of such instruments are discussed and disclosed in the copending patent application Ser. No. 208,368, filed on Nov. 19, 1980. Such instruments typically include a magazine or cartridge which may or may not be disposable and which holds a plurality of clips. The clips are supplied from the cartridge to jaws of the instrument one at a time for application to the tissue or blood vessel.

U.S. Pat. No. 3,006,344 discloses an instrument for applying a ligating clip to a blood vessel. The clip is formed of flat metal or like stock and has a pair of legs extending outwardly in a generally V-shape. The clips are arranged in two parallel grooves in a magazine. A slide is positioned in each groove and is urged by a suitable conventional spring to advance the clips along the magazine toward the jaws. The clips are arranged in each row with one end of one clip abutting the connecting rear portion of the next adjacent front clip. The clips are not nestably arranged with the connecting portion of each clip received between the open legs of the next adjacent clip. Rather, the distal end of one of the legs of one clip abuts the rear connecting portion of the next adjacent clip.

U.S. Pat. No. 3,753,438 discloses an applicator for applying clips to suturing thread during the suturing of skin wounds. The clips are carried in a cartridge in the instrument. A clip is forced forwardly from the cartridge to a position between the instrument jaws by a slide which is operated by a handle. After the clip is positioned within the jaws, the handles of the instrument are squeezed together to squeeze the clip legs together.

It would be desirable to provide an improved instrument for accommodating a plurality of clips and for automatically feeding the clips seriatim into jaws where the clips may be compressed about tissue, such as blood vessels and the like. It would be beneficial if the clips were contained within a magazine or cartridge and it would be advantageous if the magazine could be easily inserted into, and removed from, the instrument. It would also be beneficial if the instrument could accommodate a magazine of relatively simple design having relatively low material costs and low fabrication costs so that the magazine may be disposable.

It would also be desirable to provide an instrument for applying clips wherein the clips could be arranged in a relatively compact orientation in order to provide an efficient and economical magazine structure. It would be beneficial if the instrument could be provided with means for biasing the clips forwardly from the magazine to the jaws but in a manner that would prevent the clip from being urged or biased against the tissue. This would avoid imposition of an undesired force on the tissue during application of the clip. Further, elimination of a feeding force on the clip during application of the clip would reduce the possibility that the clip might twist or turn during the application of the clip to the tissue. Further, it would also be desirable to eliminate the feeding force on all of the clips in the magazine during the application of the front end clip in the jaws so as to insure that the clips within the magazine are not forced outwardly against the front end clip. This would reduce the possibility that one or more clips might twist or turn at the end of the magazine in the jaw region.

In addition, after a clip has been applied without the undesirable feeding force, it would be beneficial to permit the feeding force to then be re-established on the clips in the magazine. Further, it would be beneficial if the re-establishment of the feeding force could be done in a manner that avoids the imposition of a rapidly applied force or shock loading to the row of clips in the magazine. This would reduce the possibility of the clips being unduly compressed or of the clips twisting in the magazine.

It would also be desirable to provide an instrument for applying ligating clips in which the instrument could be actuated by means of scissors-type handles in the same manner as a number of other widely used surgical instruments and in the manner to which surgeons have become accustomed over the years.

SUMMARY OF THE INVENTION

A preferred embodiment of the present invention is incorporated in a medical instrument for applying clips, including ligating clips made from a thermoplastic material. The clips each typically have two legs connected together at one end of the clip and adapted to be opened or spread apart at the other end.

The instrument includes first and second jaws disposed in confronting relationship and mounted for pivotal movement away from each other to receive one of the clips and toward each other to close and set the one clip about the tissue. The instrument further has first and second scissors-type handles mounted for pivotal movement toward each other from an open position, wherein the first and second jaws are permitted to be opened, to a closed position for engaging and closing the first and second jaws about one of the clips so as to close the clip.

The instrument includes a magazine or cartridge that has a channel for receiving the open clips in a single row with the clips being arranged in nesting relationship so that the hinge portion of one clip is received between the distal ends of the legs of the next rearwardly adjacent clip. The magazine is disposed on the instrument so as to feed the clips forwardly between the first and second jaws with the leg connection end of each clip trailing the distal ends of the clip legs.

A pusher bar is slidably carried on the instrument and is aligned to enter into one open end of the magazine and push forwardly against the hinge portion of the last clip in the magazine. A spring is provided for biasing the pusher bar forwardly into the magazine and against the last clip in the magazine.

The pusher bar has a plurality of gear teeth along one edge. A toothed pawl is provided for engaging the teeth on the pusher bar. The pawl is pivotally mounted to one of the scissors handles forwardly of the region of engagement between the pusher bar teeth and the pawl teeth whereby movement of the scissors handles toward each other causes the pawl to engage the pusher bar and pivot in a first direction to retract the pusher bar rearwardly.

A pawl biasing spring is provided for biasing the pawl in a second direction to a forward position when the scissors handles are moved away from each other whereby the pawl permits movement of the pusher bar forwardly against the last clip in the magazine to position a clip in the jaws when the jaws are opened.

In the novel clip applier described above, the biasing force of the pusher bar on the row of clips in the magazine is terminated (by engagement of the pawl with pusher bar) each time the scissors handles are closed (when a clip is squeezed closed). This prevents an undesirable force from being transmitted through the row of clips to the clip being applied to the tissue. Elimination of the biasing force during the application of the clip reduces the possibility that the tissue, such as a blood vessel, will be damaged or moved during the application of the clip.

Further, elimination of the biasing force during the application of the clip reduces the possibility that the clip may twist or turn in the jaws of the instrument as the clip is being applied to the tissue. Also, elimination of the biasing force on the row of clips in the instrument magazine reduces the possibility that the other clips in the magazine behind the front clip will twist or turn at the end of the magazine adjacent the jaws.

In the novel clip applier of the present invention, the pusher bar is permitted to again be biased forwardly against the row of clips in the magazine when the scissors handles are subsequently opened. However, owing to the novel pawl structure described above, the pusher bar is prevented from being moved too rapidly forward under the influence of the pusher bar spring. Rather, the forward movement of the pusher bar against the clips is controlled by the rate of opening of the handles through the pawl so that the pusher bar is not forced against the last clip in the magazine with an undesirable impact. This prevents undue compression of the nested clips within the magazine and prevents twisting or turning of the clips within the magazine.

The apparatus of the present invention resides in the novel combination, construction, arrangement, and disposition of various component parts and elements incorporated in the apparatus in accordance with the principles of the invention.

The present invention will be better understood and important features other than those specifically enumerated above will become apparent when consideration is given to the following details and description which, when taken in conjunction with the drawings, describes, discloses, illustrates, and shows a preferred embodiment of the present invention and what is presently believed to be the best mode of practicing the principles of the invention. Other embodiments and modifications may be suggested to those having the benefit of the teachings herein, especially as they fall within the scope and spirit of the sub-joined claims.

BRIEF DESCRIPTION OF THE DRAWINGS

In the accompanying drawings forming part of the specification and in which like numerals are employed to designate like parts throughout the same, FIG. 1A is a perspective view of one type of surgical clip which may be applied to tissue with the instrument of the present invention;

FIG. 1B is a view similar to FIG. 1A but showing the clip latched closed;

FIG. 2 is a top plan view of the instrument of the present invention with portions of the top cover plate broken away to permit illustration of interior details;

FIG. 3 is a greatly enlarged, cross-sectional view taken generally along the plane 3—3 in FIG. 2;

FIG. 4 is a greatly enlarged, fragmentary, cross-sectional view taken generally along the plane 4—4 in FIG. 2;

FIG. 5 is a view of the front end of the instrument shown in FIG. 1 with a portion of the clip magazine broken away to better illustrate the underlying structure;

FIG. 6A is a greatly enlarged, fragmentary, cross-sectional view taken generally along the plane 6A—6A in FIG. 2;

FIG. 6B is a greatly enlarged, fragmentary, cross-sectional view taken generally along the plane 6B—6B in FIG. 2;

FIG. 7 is a view similar to FIG. 2 but with the clip magazine shown in section, with the handles shown partially closed, and with a first, open clip shown disposed within the open jaws around a blood vessel;

FIG. 8 is a view similar to FIG. 7 but showing the scissors handles fully closed and showing the jaws fully closed to latch the clip closed about the blood vessel;

FIG. 9 is a fragmentary view similar to FIG. 5 with a portion of the clip magazine broken away and showing the first clip latched closed about the blood vessel as in FIG. 8; and FIG. 10 is a view similar to FIG. 7 but showing the handles in a fully opened position with the jaws opened to release the latched closed clip.

DESCRIPTION OF THE PREFERRED EMBODIMENTS

This invention may be used in many different forms. The specification and the accompanying drawings disclose a specific embodiment as an example of the use of the invention. The invention is not intended to be limited to the embodiment illustrated, and the scope of the invention will be pointed out in the appended claims.

The precise shapes and sizes of the components herein described are not essential to the invention unless otherwise indicated. The particular shapes and sizes are shown to best illustrate the principles of the invention.

The choice of materials for constructing the illustrated apparatus is dependent upon the particular application involved and other variables, as those skilled in the art will appreciate.

One type of clip or clamp that may be applied with the instrument of the present invention is shown in FIG. 1A and 1B and is designated therein generally by the reference numeral 10. The clip 10 is seen to be formed with two legs or leg segments 11 and 12 which are joined at the leg connection end of the clip. Preferably, the legs are connected at the proximal ends thereof by a hinge, a hinge portion, or a hinge section 13. The leg segment 11 terminates at the distal end thereof in a hook member 14 having an inner face 15 substantially parallel to an inner face 16 of the leg segment 11 and forming an acute angle with an end face 17.

The leg segment 12 terminates at the distal end in an end face 19 which forms an obtuse angle with an inner face 18 of the leg segment 12. The end face 19 is offset at 23 to form a notch approximately midway between the inner face 18 and a bottom face 20. Additionally, the leg segment 12 is squared off at a face 25 to form a substantially right angle with the bottom face 20.

The length and width of the inner faces 16 and 18 are substantially equal and the face 15 of the hook member 14 is spaced from the inner face 16 of the leg segment 11 by a distance corresponding to the thickness of the leg segment 12 between the planes of the inner face 18 and the bottom face 20.

The clip 10 can be closed or set by pivoting the leg segments 11 and 12 about the hinge section 13 to bring the inner faces 18 and 16 into opposition. The hook member 14 is deflected by the end face 19 of the leg segment 12 until the distal end of the leg segment 12 snaps under the hook member 14 and is thereby locked in place as best illustrated in FIG. 1B. The end face 17 of the hook member 14 and the end face 19 of the leg segment 12 are angled as illustrated in FIG. 1A to facilitate the passage of the leg segment 12 past the hook member 14 during clip closure.

The surfaces of the inner faces 16 and 18 may be smooth as illustrated in FIG. 1A, or may be provided with ridges or grooves to increase vessel holding power. The leg segment 11 may also be undercut at the juncture of the hook member 14 and the inner face 16 as illustrated in FIGS. 1A and 1B to increase the deflectability of the hook member 14 and increase the space between the hook member 14 and the leg segment 11. This compensates for any inward deflection of the hooked member 14 during closure which might reduce the clearance between the surfaces 15 and 16 and otherwise interfere with the latching of the clip.

With continued reference to FIGS. 1A and 1B, the leg segment 12 of the clip 10 includes an outside cylindrical boss 21 extending across the width of the leg segment 12 near the distal end thereof. Similarly, the leg segment 11 has a boss 22 extending across the width of the leg segment 11 near the distal end thereof. The cylindrical bosses 21 and 22 are equidistant from the hinge section 13 so that when the clip 10 is closed, the bosses 21 and 22 define a line perpendicular to the major axis along the length of the clip as best illustrated in FIG. 1B. The boss 21 is spaced from the face 25 a distance sufficient to permit the full engagement of the hook member 14 by the leg segment 12 when the clip 10 is in the closed and latched position.

The distal end of the leg segment 12 forward of the boss 21 is of reduced thickness relative to the thickness immediately to the rear of the boss 21, thereby forming a step 24 between the boss 21 and the botton surface 20.

The above-described novel clip structure, when fabricated from a suitable thermoplastic material, is biased to the open position by the resilient hinge portion. Thus, if force is applied to the distal ends of the legs of the open clip so as to move the legs toward one another (but not far enough to latch the clip), then upon removal of the force from the clip legs, the clip legs will return to the substantially fully open orientation.

It is believed that this phenomenon can be used to advantage in certain types of clip applier instruments for guiding and holding the clip in the instrument. Specifically, the legs of the clip may be deflected inwardly toward one another a small amount in a magazine, guide channel, or jaw structure of a clip applier instrument. Owing to the resilience of the hinge joining the two legs, the two legs will exert a force outwardly against the magazine, channel, or jaw structure to thereby provide a small friction holding force which may serve to help maintain the clip in the proper orientation or position within the instrument.

The above-described action of the resilient hinge plastic clip is in contrast with conventional ligating clips fabricated from relatively small diameter wire-like stock. Such metal clips can tolerate substantially no inward deflection of the legs without undergoing permanent deformation. Consequently, such metal clips exhibit no useful degree of resiliency and thus do not have the same inherent capability for providing the frictional holding force that is found in the above-described type of plastic clip.

FIG. 2 illustrates one form of an instrument 30 of the present invention for applying clips, such as the ligating clip 10 described above with reference to FIGS. 1A and 1B. The instrument 30 includes a bottom carrier plate or frame 32 and a top cover plate 34. The top cover plate 34 may be secured to upstanding rib portions 36 of the lower frame or plate 32 by screws, such as screw 35 shown extending into a rib portion 36 of the plate 32.

A first scissors-type handle 41 is pivotally mounted about pin 43 between the plates 32 and 34 and a second scissors-type handle 42 is pivotally mounted about a pin 44 between the carrier plates 32 and 34. the first handle 41 has an engaging end portion 45 forwardly of the pivot pin 43 and the second handle 42 has an engaging end portion 47 forwardly of the pivot pin 44.

Forwardly of the scissors handles 41 and 42 are a pair of actuating members, first actuating member 51 and second actuating member 52. The first actuating member 51 is pivotally mounted to the bottom carrier plate 32 by means of a pin 53 and has a portion 54 extending rearwardly from the pin 53 and a forward distal end portion or jaw engaging portion 56 that extends forwardly of the pin 53.

The second actuating member 52 is pivotally mounted to the bottom carrier plate 32 by pin 57 and has a portion 58 extending rearwardly of pin 57 and a forward distal end portion or jaw engaging portion 59 that extends forwardly of pin 57.

As best illustrated in FIG. 5, a first jaw 61 is pivotally mounted to the bottom carrier plate 32 about a pin 63. A second jaw 62 is pivotally mounted to the bottom carrier plate 32 about a pin 64. The forward distal end of jaw 61 has an inwardly extending lip 65 and the forward distal end of the jaw 62 has an inwardly extending lip 67. The forward distal ends of the first and second jaws 61 and 62, respectively, are biased outwardly to an opened position by a spring 69 disposed between the jaws 61 and 62.

In the opened position illustrated in FIG. 5, the first jaw 61 bears against the jaw engaging portion 56 of the first actuating member 51. Similarly, the second jaw 62 bears against the jaw engaging portion 59 of the second actuating member 52. When the jaws 61 and 62 are in the opened position illustrated in FIG. 5, the actuating members 51 and 52 are aligned in a generally parallel orientation. The spring 69 has a configuration that biases the jaws 61 and 62, and hence the actuating members 51 and 52, to the parallel positions illustrated in FIG. 5 but not outwardly beyond those positions.

A plurality of clips 10 are carried in the instrument and are automatically fed to the first and second jaws 61 and 62, respectively. To this end, a cartridge or magazine 70 is releasably mounted on the carrier plate 32 as best illustrated in FIGS. 2, 3, and 4. As best illustrated in FIG. 4, the magazine 70 has a generally C-shaped cross section defining a channel 72 for receiving the open clips 10 in a single row.

The magazine 70 is preferably supported at one end by a pair of spaced-apart clamp members 74 as best illustrated in FIGS. 3 and 4. As best illustrated in FIG. 4, each clamp member 74 extends upwardly from the bottom carrier plate 32 and has a first or lower bead or shoulder 76 and a second or upper bead or rounded shoulder 78. The clamp members 74 are sufficiently resilient to permit insertion and removal of the magazine 70. Specifically, the magazine 70 may be lifted upwardly out of the instrument. The upward force on the magazine 70, as it is being lifted upwardly out of the instrument, acts upon the upper, rounded shoulder 78 of each clamp member 74 to deflect each clamp member 74 outwardly to permit removal of the magazine 70.

Typically, after an empty magazine 70 is removed from the instrument, a new magazine 70, full of clips 10, is inserted in the instrument by pushing the new magazine 70 downwardly against the rounded shoulders 78 of the clamp members 74. This deflects the clamp members 74 outwardly an amount sufficient to accommodate the insertion of the magazine 70 between the clamp members 74. Insertion of the magazine 70 into the instrument is limited by the first or lower shoulders or beads 76. When the magazine 70 is properly inserted in the instrument, the magazine 70 is held between the clamp members 74 and is restrained against downward movement by the first or lower shoulders 76 and against upward movement by the second or upper shoulders 78.

With reference to FIGS. 2, 3 and 5, it can be seen that the forward end of the magazine 70 rests upon the top surfaces of the first and second jaw pivot pins 63 and 64, respectively. The clamp members 74, rearwardly of the pivot pins 63 and 64, have sufficient gripping or clamping power so as to prevent movement of the mgagazine within the clamp members 74 in the longitudinal direction along the length of the instrument.

The clips 10 are maintained in a single row in the magazine 70 with the clips being arranged in a nesting relationship. The leg connection end or hinge of one clip is received between the distal ends of the open legs of the next rearwardly adjacent clip. The magazine 70 is disposed in the instrument so as to feed the clips forwardly to the jaws 61 and 62 with the hinge of each clip trailing the distal ends of the clip legs.

The magazine 70 is designed in a way that permits the magazine to be easily loaded with clips 10. Specifically, before the magazine 70 is inserted into the instrument 30, a row of clips can be loaded into the empty magazine from either open end of the magazine. Preferably, the width of the channel 72 (FIG. 4) of the magazine 70 is slightly less than the width of an opened clip 10. Accordingly, a row of clips 10 may be inserted, hinge end first, into the magazine 70 and the legs of the clips will be forced inwardly a small amount by the walls of the magazine. Owing to the resilient nature of the hinge portion or hinge end of each clip 10, the legs of each clip are biased outwardly against the magazine 70 and serve to maintain the clips within the magazine. This permits the magazine 70 to be pre-loaded with clips, stored, and subsequently handled as may be necessary until the magazine is loaded into an instrument 30.

Once the full magazine 70 is properly loaded or positioned within the instrument 30, the instrument is operated to move one clip at a time into the instrument jaws 61 and 62. FIG. 2 illustrates the front clip of the row of clips in place in the jaws 61 and 62. The front clip is retained against further forward movement by the inwardly extending lips 65 and 67 of the first and second jaws 61 and 62, respectively. Movement of the row of clips 10 forwardly along the magazine during operation of the instrument 30 is effected by a novel mechanism that is described next in detail.

As best illustrated in FIGS. 2, 3, and 6A, a guide or guide structure 80 extends from or is mounted to the bottom carrier plate 32. The guide 80 extends longitudinally behind the magazine 70 and is aligned with, or is in registry with, the magazine 70. As best illustrated in FIG. 6A, the guide 80 includes a pair of spaced-apart walls 82 that extend upwardly from the bottom carrier plate 32. The walls 82 are joined by a central cross wall 84 which defines therein a slot 86 extending the length of the guide 80. Each wall 82, at its upper or distal end, has an inwardly projecting flange or lip 88. The lips 88 are spaced outwardly from, or above, the cross wall 84.

A guide channel 90 is defined by the sidewalls 82, the cross wall 84, and the lips 88. The guide channel 90 is adapted for receiving an elongate member or pusher bar 100. The pusher bar 100 has a generally rectangular cross section and has teeth 101 extending on one side along the length of the bar. The pusher bar 100 is slidably disposed within the guide channel 90 and is adapted to slide forwardly and project into the channel 72 of the magazine 70 as best illustrated in FIG. 2. To this end, the channel 90 of the guide 80 and the channel 72 of the magazine 70 are substantially identical in cross-sectional size and shape and are in substantial alignment or registry.

The pusher bar 100 is biased forwardly in the guide 80 by means of a Hunter type constant force spring 102 as best illustrated in FIG. 3. Specifically, the spring 102 has a coiled portion 104 encircling and mounted to a post 106 that projects upwardly from the bottom carrier plate 32. The uncoiled portion of the spring 102 extends along the length of the instrument beneath the pusher bar 100 and is secured to a post or pin 110 which projects downwardly from the pusher bar 100 at the rearward end of the pusher bar 100. As best illustrated in FIG. 6A, the pin 110 projects through the slot 86 of the cross wall 84 of the guide 80. Thus, the spring 102 can urge the pusher bar 100 to move forwardly along the length of the guide 80. This causes the forward distal end of the pusher bar 100 to contact the last clip in the magazine 70 and to push the row of clips forward in the magazine until the front clip is received in the first and second jaws 61 and 62, respectively.

As best illustrated in FIGS. 2, 6A, and 6B, a novel means is provided for temporarily interrupting the forward biasing of the pusher bar 100. Specifically, a toothed pawl 150 is carried on the scissors-type handle 41. The handle 41 is provided with a cut out portion or receiving well 152 in which one end of the pawl 150 is disposed. The pawl 150 is pivotally mounted to the scissors-type handle 41 in the receiving well 152 by means of a pin or post 154 which projects upwardly from the bottom of the receiving well 152.

As best illustrated in FIGS. 2 and 6B, it is seen that the pawl 150 is biased to a forward position by means of a wire torsion spring 160. The spring 160 is disposed around the pin 154 and has one end 162 engaging the scissors-type handle 41 and has another end 164 engaging the rearward side of the pawl 150.

The pawl 150 has an arcuate configuration and is provided with a plurality of teeth 170 along one side. The teeth 170 of the pawl 150 are adapted to engage the teeth 101 of the pusher bar 100. To this end, the pusher bar guide 80 is provided with an opening or slot 179 along one side as best illustrated in FIGS. 2 and 3 to permit engagement of the pawl 150 with the pusher bar 100.

The operation of the instrument 30 will next be described with reference to FIGS. 7–10. In FIG. 7, the instrument 30 is shown applying a clip to a blood vessel 180. A front clip of the row of clips in the magazine 70 is in position between the first and second jaws 61 and 62, respectively. The legs of the front clip are open and positioned on either side of the blood vessel 180. The instrument handles 41 and 42 are partially closed, but not enough to cause actuation of the jaws 61 and 62. In this position, the pawl 150 is engaged with the pusher bar 100.

As the scissors-type handles 41 and 42 are squeezed together as illustrated in FIG. 8, the pawl 150 pivots in a first direction (clockwise as viewed in FIG. 8) to keep the teeth of the pawl 150 in engagement with the teeth 101 of the pusher bar 100. There is a slight rearward movement of the pusher bar 100 (away from the clips in the magazine 70) as the scissors-type handles 41 and 42 are squeezed closed. The withdrawal of the pusher bar 100 is illustrated in FIG. 8 wherein the clip engaging end of the pusher bar 100 is illustrated as having been moved rearwardly a distance x from the last chip in the magazine 70. This removes the biasing force from the row of clips in the magazine 70. When the biasing force is removed from the row of clips in the magazine 70, the legs of each clip remain outwardly biased against the walls of the magazine 70 and the clips are thus still maintained in position in the magazine.

As the handles 41 and 42 are squeezed closed, the forward engaging portion of each handle engages the rearwardly extending portion of the associated actuating member (members 51 and 52). This causes the actuating members 51 and 52 to pivot. As illustrated in FIG. 9, the forward distal end 56 of the actuating member 51 contacts the first jaw 61 forward of the pivot pin 63. Similarly, the forward distal end portion 59 of the actuating member 52 engages the second jaw 62 forward of the pin 64. This causes the jaws 61 and 62 to pivot about the pivot axes defined by the pivot pins 63 and 64. The jaws 61 and 62 thus pivot toward each other—away from the open position to the closed position as illustrated in FIG. 8.

As the jaws 61 and 62 are pivoted closed, the front clip 10 positioned between the jaws is squeezed closed about the blood vessel 180. The closed clip 10 remains closed owing to the latch structure described above in detail with reference to the clip design illustrated in FIGS. 1A and 1B.

The jaws 61 and 62 must next be permitted to open, under the influence of the jaw spring 69 (FIGS. 5 and 9), so as to facilitate removal of the instrument 30 from the blood vessel 180 which is now strangulated with the closed ligating clip 10. To this end, the scissors-type handles 41 and 42 are opened by the surgeon as best illustrated in FIG. 10. As soon as the scissors-type handles 41 and 42 have been opened far enough (at least to the orientation illustrated in FIG. 7), the jaw spring 69 is able to bias the jaws 61 and 62, as well as the actuating members 51 and 52, to the generally parallel, opened positions illustrated in FIG. 7. This allows the jaws 61 and 62 to clear the closed clip 10 and blood vessel 180.

Further outward movement of the scissors-type handles 41 and 42, to the position illustrated in FIG. 10, lifts the pawl pivot post 154 outwardly away from the pusher bar 100. This permits the pawl 150 to pivot forwardly and permits the pusher bar 100 to be biased forwardly (by the spring 102 described above with reference to FIG. 3) against the last clip in the row of clips in the magazine 70. This causes the clips to be pushed forwardly within the magazine until the new front clip in the row is properly positioned in the jaws 61 and 62.

In the position illustrated in FIG. 10, the handles 41 and 42 are sufficiently far apart to permit the pawl spring 160 to rotate the pawl 150 back in a second direction (counterclockwise as viewed in FIG. 10) until a portion of the pawl engages the edge of the handle 41 as illustrated at point 190 in FIG. 10. This point 190 on the handle 190 functions as a stop to limit the amount of rotation of the pawl 150.

When the handles are in the extreme open position as is illustrated in FIG. 10, it is essential that the teeth of the pawl 150 be disengaged from the teeth of the bar 100 to permit the pawl to pivot all the way forward again. Further, it is essential that the pawl 150 engage the bar 100 when the handles are subsequently closed so as to interrupt or terminate the biasing force on the row of clips in the magazine. This prevents an undesirable force from being transmitted through the row of clips to the front clip being applied to the vessel. Further, elimination of the biasing force during the application of the clip reduces the possibility that the vessel will be damaged or moved during the application of a clip. Further, elimination of the biasing force during the application of the clip reduces the possibility that the clip may twist or turn in the jaws of the instrument as the clip is being applied to the tissue. Also, elimination of the biasing force on the row of clips in the instrument magazine reduces the possibility that the other clips in the magazine behind the front clip will twist or turn at the end of the magazine adjacent the jaws.

When the pawl 150 engages the pusher bar 100 during closure of the instrument handles, it is essential only that the pusher bar 100 be moved rearwardly only a small amount sufficient to relieve the force on the row of clips in the magazine 70. The amount of rearward movement may be so small as to not be visible to the unaided eye.

However, regardless of how far the pusher bar 100 is moved rearwardly during the closure of the handles 41 and 42, it is desirable to avoid the imposition of a sudden shock loading or force on the row of clips in the magazine 70 when the handles are subsequently opened. A sudden shock loading or imposition of a sudden force on the row of clips, caused by the pusher bar 100 being forced rapidly against the last clip in the magazine by the spring 102, may cause the clips to be unduly compressed and/or may cause the clips to twist, turn, or buckle within the magazine or at the region of the jaws 61 and 62. The structure and arrangement of the novel pawl 150 prevents the imposition of such a suddenly applied impact force to the clips in the magazine 70 as will next be explained.

Specifically, as the handles 41 and 42 are opened, the teeth on the pawl 150 initially remain engaged with the teeth on the pusher member 100. The rotation of the pawl 150 forwardly toward the jaws is governed by the speed of the opening of the handles 41 and 42. Even the most rapid opening movement by the human hand is not fast enough to cause any undesirable shock loading of the clips in the magazine 70. As soon as the front of the pusher bar has contacted the last clip in the magazine 70, the pawl 150 can be completely disengaged from the pusher bar 100, by further outward movement of handles 41 and 42, to permit the pawl 150 to rotate to the forward position illustrated in FIG. 10.

As best illustrated in FIG. 10, the handles 41 and 42 can be opened until the forward engaging portions 45 and 47, respectively, engage the sides of the magazine 70. Any other suitable travel limit or stop structure may be provided if desired.

As can be seen by comparing FIGS. 7 and 10, each time a clip is applied with the instrument 30, the pusher bar 100 is moved forwardly an incremental distance equal to the distance between adjacent clips (as measured from the forward ends of the legs of one clip to the forward ends of the legs of the next rearwardly adjacent clip). The pusher bar 100 thus moves intermittently forward into the magazine as the clips are being applied and eventually the forward end of the pusher bar 100 hits the first and second jaws 61 and 62. At this point, an attempt to squeeze the jaws 61 and 62 will be unsuccessful since the pusher bar 100 resists inward movement of the jaws. This signals the surgeon that all of the clips have been used. Of course, the surgeon can easily monitor the number of clips remaining in the instrument at any time since the clips 10 are visible in the magazine 70.

After all of the clips have been applied with the instrument 30, a person may move the pusher bar 100 with his finger rearwardly a distance sufficient to retract it completely from the magazine. This will permit the person to remove the magazine 70 from the instrument 30 and insert a new, full magazine into the instrument. The empty magazine may be then refilled with clips in a manner previously described in detail.

In the preferred form of the invention, the magazine 70 is releasably mounted in the instrument as described above. However, it is to be realized that the magazine may be permanently secured to the instrument if desired. With a fully disposable instrument, there would be no need for a removable magazine.

Although the pawl 150 is illustrated as being pivotally mounted about post 154, it is to be realized that the pawl 150 need not be mounted about a post for rotation relative thereto. Rather, the pawl may be a resilient member projecting from the handle 41. The pawl would have sufficient flexibility to accommodate the degree of "pivoting" movement necessary during the closure of the handle 41.

The instrument of the present invention may be used to apply other types of clips, including metal hemostatic clips, that are utilized in surgical procedures. For example, such clips may be narrow U-shaped or V-shaped strips formed of tantalum or stainless steel which are capable of being deformed and which possess sufficient strength to retain the deformation when clamped about a duct, such as a blood vessel.

From the foregoing, it will be observed that numerous variations and modifications may be effected without departing from the true spirit and scope of the novel concept of the invention. It is to be understood that no limitation with respect to the specific apparatus illustrated herein is intended or should be inferred. It is, of course, intended to cover by the appended claims all such modifications as fall within the scope of the claims.

It is claimed:

1. A repeating scissors-type medical instrument for applying a plurality of ligating clips seriatim about tissue wherein each said clip is initially provided in an open state, each said open clip comprising first and second legs joined at their proximal ends by a resilient hinge and being spaced apart at their distal ends with said legs having latch means at said distal ends for holding said clip closed in clamping engagement about said tissue when said legs are squeezed together, said instrument comprising:

first and second jaws disposed in confronting relationship and mounted for pivotal movement away from each other into an opened position to receive one of said clips and toward each other into a closed position for closing and latching said one clip;

first and second scissors-type handles for operating said jaws, said scissors-type handles being mounted to said instrument for pivoting toward each other from an open position wherein said jaws can be opened to a closed position for effecting movement of said jaws to said closed position;

a magazine defining a channel for receiving said open clips in a single row with the clips arranged in nesting relationship with the hinge of one clip being received between the distal ends of the legs of a next rearwardly adjacent clip, said magazine disposed on said instrument to feed said clips forwardly to said jaws with the hinge of each clip trailing the distal ends of the clip legs;

a pusher bar slidably carried on said instrument and aligned to enter into one end of said magazine and push forwardly against the last clip in the magazine, said bar defining a plurality of teeth along a portion of the length of the bar;

pusher bar biasing means for biasing said pusher bar forwardly into said magazine and against the last clip in said magazine; and a toothed pawl for engaging said teeth on said pusher bar, said pawl being mounted to one of said handles forwardly of the region of engagement between said pusher bar teeth and said pawl so as to accommodate pivoting movement whereby movement of said handles toward each other causes the pawl to engage said pusher bar and pivot in a first direction to disengage said pusher bar from the last clip in said magazine and whereby movement of said handles away from each other permits the pawl to be pivoted in a second direction by the movement of said pusher bar forwardly on said instrument against the last clip in the row in said magazine under the influence of said pusher bar biasing means to position the front clip in the row at the opened jaws.

2. The instrument in accordance with claim 1 further including a pawl biasing means for biasing said pawl in said second direction to a fully forward position when said handles are moved away from each other.

3. The instrument in accordance with claim 1 in which each of said first and second jaws is pivotally mounted to a carrier plate.

4. The instrument in accordance with claim 3 further including jaw biasing means for biasing said jaws outwardly away from each other into said opened position.

5. The instrument in accordance with claim 3 in which each of said first and second jaws includes an inwardly projecting lip portion for limiting the forward movement of a clip beyond said jaws.

6. The instrument in accordance with claim 1 further including a pair of pivotally mounted actuating members, each said actuating member having a forward distal end portion adapted to engage one of said jaws forwardly of the pivot axis of said actuating member and having a rear portion extending beyond the pivot axis of said actuating member and adapted to be engaged by a portion of one of said first and second scissors-type handles.

7. The instrument in accordance with claim 6 in which each of said first and second scissors-type handles includes an engaging portion extending beyond the pivot axis of the handle and adapted to engage said rearwardly extending portion of one of said actuating members whereby, when said first and second scissors-type handles are moved toward each other, said engaging portion of each of said first and second scissors-type handles moves outwardly to engage said rearwardly extending portion of one of said actuating members to pivot said actuating members and force said forward distal end portions of said actuating members against one of said first and second jaws to thus pivot said jaws toward each other from said opened position to said closed position.

8. The instrument in accordance with claim 7 in which said first and second scissors-type handles and said first and second actuating members are pivotally mounted to a carrier plate.

9. The instrument in accordance with claim 1 in which said pawl is pivotally mounted to one of said scissors-type handles rearwardly of the pivot axis of said one scissors-type handle.

10. The instrument in accordance with claim 1 in which said pawl has an arcuate array of teeth.

11. The instrument in accordance with claim 1 in which said magazine is mounted to a carrier plate and which said pusher bar biasing means includes a Hunter type constant force coil spring mounted to said carrier plate and connected at one end to said pusher bar whereby said pusher bar is biased forwardly in said magazine under the influence of said Hunter type spring.

12. The instrument in accordance with claim 1 in which said magazine has a pair of inwardly projecting flanges extending over a portion of the distal end of each of said legs of each of said clips in said magazine to contain said clips within said magazine.

13. The instrument in accordance with claim 1 in which said magazine has an open rear end to admit said pusher bar and an open front end to permit the discharge of said clips.

14. The instrument in accordance with claim 1 including a carrier plate, said pusher bar biasing means being mounted on said carrier plate, said instrument further including means being mounted to said carrier plate for slidably supporting and guiding said pusher bar above said carrier plate and further including a member projecting downwardly from said pusher bar and secured to said pusher bar biasing means.

15. The instrument in accordance with claim 1 wherein said pawl is biased toward said second direction by a torsion spring.

16. The instrument in accordance with claim 1 wherein said magazine is releasably mounted to said instrument.

17. A repeating scissors-type medical instrument for applying a plurality of ligating clips seriatim about tissue wherein each said clip is initially provided in an open state, each said open clip comprising first and second legs joined at their proximal ends by a resilient hinge and being spaced apart at their distal ends with said legs having latch means at said distal ends for holding said clip closed in clamping engagement about said tissue when said legs are squeezed together, said instrument comprising:

a frame;

first and second jaws disposed in confronting relationship and mounted to said frame for pivotal movement away from each other into an opened position to receive one of said clips and toward each other into a closed position for closing and latching said one clip;

jaw biasing means for biasing said jaws outwardly away from each other into said opened position;

a pair of actuating members pivotally mounted to said frame, each said actuating member having a forward distal end portion adapted to engage one of said jaws forwardly of the pivot axis of said actuating member and having a rear portion extending beyond the pivot axis of said actuating member;

first and second scissors-type handles mounted to said frame for pivotal movement, each of said first and second scissors-type handles including an engaging portion extending beyond the pivot axis of the scissors-type handle and adapted to engage said rearwardly extending portion of one of said actuating members whereby, when said first and second scissors-type handles are moved toward each other, said engaging portion of each of said first and second scissors-type handles moves outwardly to engage said rearwardly extending portion of one of said actuating members to pivot said actuating members and force said forward distal end portions of said actuating members against said first and second jaws to thus pivot said jaws toward each other from said opened position to said closed position;

a magazine releasably mounted on said frame and defining a channel for receiving said open clips in a single row with the clips arranged in nesting relationship with the hinge of one clip being received between the distal ends of the legs of a next rearwardly adjacent clip, said magazine disposed on said instrument to feed said clips forwardly to said jaws with the hinge of each clip trailing the distal ends of the clip legs;

a guide mounted to said frame and defining a guide channel in registry with said magazine channel;

a pusher bar disposed in said guide channel and slidably carried by said guide on said instrument, said pusher bar being adapted to extend from one end of said guide channel and enter into one end of said magazine channel to push forwardly against the last clip in the magazine, said pusher bar further defining a plurality of gear teeth along one side;

pusher bar biasing means for biasing said pusher bar forwardly into said magazine and against the last clip in said magazine;

a toothed pawl for engaging said teeth on said pusher bar, said pawl being pivotally mounted to one of said handles forwardly of the region of engagement between said pusher bar teeth and said pawl whereby movement of said handles toward each other causes the pawl to engage said pusher bar and pivot in a first direction to retract said pusher bar from said engagement with said clips and whereby movement of said handles away from each other permits the pawl to be pivoted in a second direction by the movement of said pusher bar forwardly on said instrument against the last clip in the row in said magazine under the influence of said pusher bar biasing means to position the front clip in the row at the opened jaws; and pawl biasing means for biasing said pawl in a second direction to a fully forward position when said handles are moved away from each other.

18. A repeating scissors-type medical instrument for applying a plurality of ligating clips seriatim about tissue wherein each said clip is initially provided in an open state, each said open clip comprising first and second legs joined at their proximal ends by a resilient hinge and being spaced apart at their distal ends, said clip legs having latch means at said distal ends for holding said clip closed in clamping engagement about said tissue when said legs are squeezed together, and wherein the clips are provided to the instrument in a removable, open-ended, magazine defining a channel for receiving said open clips in a single row with the clips arranged in nesting relationship with the hinge of one clip being received between the distal ends of the legs of a next rearwardly adjacent clip, said magazine adapted to be disposed on said instrument to permit said clips to be fed forwardly along said instrument in the magazine with the hinge of each clip trailing the distal ends of the clip legs; said instrument comprising:

first and second jaws disposed in confronting relationship and mounted for pivotal movement away from each other into an opened position to receive one of said clips and toward each other into a closed position for closing and latching said one clip;

first and second scissors-type handles for operating said jaws, said scissors-type handles being mounted to said instrument for pivoting toward each other from an open position wherein said jaws can be opened to a closed position for effecting movement of said jaws to said closed position;

a pusher bar slidably carried on said instrument and aligned to enter into one end of said magazine and push forwardly against the last clip in the magazine, said bar defining a plurality of teeth along a portion of the length of the bar;

pusher bar biasing means for biasing said pusher bar forwardly into said magazine and against the last clip in said magazine; and a toothed pawl for engaging said teeth on said pusher bar, said pawl being mounted to one of said handles forwardly of the region of engagement between said pusher bar teeth and said pawl so as to accommodate pivoting movement whereby movement of said handles toward each other causes the pawl to engage said pusher bar and pivot in a first direction to disengage said pusher bar from the last clip in said magazine and whereby movement of said handles away from each other permits the pawl to be pivoted in a second direction by the movement of said pusher bar forwardly on said instrument against the last clip in the row in said magazine under the influence of said pusher bar biasing means to position the front clip in the row at the opened jaws.

19. A repeating scissors-type medical instrument for applying a plurality of ligating clips seriatim about tissue wherein each said clip is initially provided in an open state, each said open clip comprising first and second legs which are joined at a leg connection end of the clip and which are spaced apart at their distal ends, and wherein the clips are provided to the instrument in a removable, open-ended, magazine defining a channel for receiving said open clips in a single row with the clips arranged in nesting relationship with the leg connection end of one clip being received between the distal ends of the open legs of a next rearwardly adjacent clip, said magazine adapted to be disposed on said instrument to permit said clips to be fed forwardly along said instrument in the magazine with the leg connection end of each clip trailing the distal ends of the clip legs; said instrument comprising:

first and second jaws disposed in confronting relationship and mounted for pivotal movement away from each other into an opened position to receive one of said clips and toward each other into a closed position for closing said one clip;

first and second scissors-type handles for operating said jaws, said scissors-type handles being mounted to said instrument for pivoting toward each other from an open position wherein said jaws can be opened to a closed position for effecting movement of said jaws to said closed position;

a pusher bar slidably carried on said instrument and aligned to enter into one end of said magazine and push forwardly against the last clip in the magazine, said bar defining a plurality of teeth along a portion of the length of the bar;

pusher bar biasing means for biasing said pusher bar forwardly into said magazine and against the last clip in said magazine; and a toothed pawl for engaging said teeth on said pusher bar, said pawl being mounted to one of said handles forwardly of the region of engagement between said pusher bar teeth and said pawl so as to accommodate pivoting movement whereby movement of said handles toward each other causes the pawl to engage said pusher bar and pivot in a first direction to disengage said pusher bar from the last clip in said magazine and whereby movement of said handles away from each other permits the pawl to be pivoted in a second direction by the movement of said pusher bar forwardly on said instrument against the last clip in the row in said magazine under the influence of said pusher bar biasing means to position the front clip in the row at the opened jaws.

* * * * *